(12) United States Patent
Huszár et al.

(10) Patent No.: US 9,249,119 B2
(45) Date of Patent: Feb. 2, 2016

(54) PROCESS FOR THE PREPARATION OF DRONEDARONE BY OXIDATION OF A SULPHENYL GROUP

(71) Applicant: SANOFI, Paris (FR)

(72) Inventors: Csaba Huszár, Budapest (HU); Adrienn Hegedus, Budapest (HU); Zsolt Dombrády, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/376,832

(22) PCT Filed: Feb. 1, 2013

(86) PCT No.: PCT/HU2013/000009
§ 371 (c)(1),
(2) Date: Aug. 5, 2014

(87) PCT Pub. No.: WO2013/121234
PCT Pub. Date: Aug. 22, 2013

(65) Prior Publication Data
US 2015/0031902 A1    Jan. 29, 2015

(30) Foreign Application Priority Data
Feb. 14, 2012    (EP) .................... 12462005

(51) Int. Cl.
*C07D 307/80*    (2006.01)
*C07D 307/82*    (2006.01)
*C07D 307/08*    (2006.01)

(52) U.S. Cl.
CPC ............ *C07D 307/80* (2013.01); *C07D 307/08* (2013.01)

(58) Field of Classification Search
CPC .......................... C07D 307/80; C07D 307/82
See application file for complete search history.

(56) References Cited

U.S. PATENT DOCUMENTS

| | | | |
|---|---|---|---|
| 3,577,441 A | 5/1971 | Kaminsky et al. | |
| 3,657,350 A | 4/1972 | Mooradian et al. | |
| 3,937,737 A | 2/1976 | Eiglmeier | |
| 4,243,405 A | 1/1981 | Balasubramanyan et al. | |
| 4,666,931 A | 5/1987 | Ohishi et al. | |
| 5,066,803 A | 11/1991 | D'Ambra et al. | |
| 5,223,510 A | 6/1993 | Gubin et al. | |
| 6,555,697 B1 | 4/2003 | Schlama | |
| 6,828,448 B2 | 12/2004 | Fino et al. | |
| 6,846,936 B2 | 1/2005 | Biard | |
| 6,855,842 B1 | 2/2005 | Schlama et al. | |
| 6,949,583 B2 | 9/2005 | Assens et al. | |
| 6,984,741 B2 | 1/2006 | Magerlein | |
| 7,148,240 B2 | 12/2006 | Assens et al. | |
| 7,312,345 B2 | 12/2007 | Gutman et al. | |
| 7,517,876 B2 | 4/2009 | Klein et al. | |
| 8,143,269 B2 | 3/2012 | Whitten et al. | |
| 8,501,971 B2 | 8/2013 | Friesz et al. | |
| 8,658,808 B2 | 2/2014 | Kretzschmar et al. | |
| 8,658,809 B2 | 2/2014 | Friesz et al. | |
| 8,674,121 B2 | 3/2014 | Kretzschmar et al. | |
| 8,686,180 B2 | 4/2014 | Bon et al. | |
| 8,748,636 B2 | 6/2014 | Bailly et al. | |
| 8,796,489 B2 | 8/2014 | Bailly et al. | |
| 8,816,103 B2 | 8/2014 | Friesz et al. | |
| 8,871,956 B2 | 10/2014 | Bailly et al. | |
| 8,884,033 B2 | 11/2014 | Bon et al. | |
| 8,889,734 B2 | 11/2014 | Friesz et al. | |
| 8,962,869 B2 | 2/2015 | Grimaud et al. | |
| 9,024,046 B2 | 5/2015 | Friesz et al. | |
| 2008/0033209 A1 | 2/2008 | Szarvas et al. | |
| 2010/0273764 A1* | 10/2010 | Andrews et al. | ........... 514/210.2 |
| 2013/0023678 A1 | 1/2013 | Priem et al. | |
| 2013/0109868 A1 | 5/2013 | Friesz | |
| 2014/0018553 A1 | 1/2014 | Grimaud et al. | |
| 2014/0081035 A1 | 3/2014 | Friesz et al. | |
| 2014/0114081 A1 | 4/2014 | Friesz et al. | |
| 2015/0005515 A1 | 1/2015 | Friesz et al. | |
| 2015/0018568 A1 | 1/2015 | Friesz | |
| 2015/0031901 A1 | 1/2015 | Bon et al. | |

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

Denmark, Scott. Angew. Chem. Int. Ed. (2008) 1560-1638.*

(Continued)

*Primary Examiner* — Golam M M Shameem
*Assistant Examiner* — Laura Daniel
(74) *Attorney, Agent, or Firm* — Morrison & Foerster LLP

(57) ABSTRACT

The invention relates to a novel process for the preparation of dronedarone (I) and pharmaceutically acceptable salts thereof which comprises oxidizing a compound of formula (IV) or a salt thereof with an oxidizing agent in an organic or inorganic solvent or solvent mixture, and isolating the obtained product and, if desired, converting it into a pharmaceutically acceptable salt thereof. Further aspects of the invention include the novel intermediary compound of formula (IV), and a process for the preparation thereof.

10 Claims, No Drawings

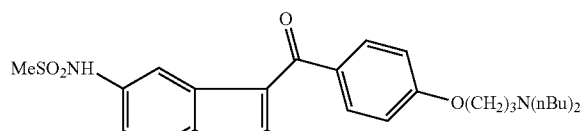

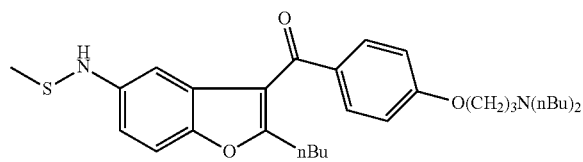

(56) References Cited

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO-02/48078 A1 | 6/2002 |
| WO | WO-02/48132 A1 | 6/2002 |
| WO | WO-03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Douglass, I.B. (1959). "Some New Reactions of Methanesulfenyl Chloride," *Journal of Organic Chemistry* 24:2004-2006.

Gilow, H.M. et al. (Jun.-Jul. 1991). "Sulfenylation of Some Pyrroles and Indoles," *J. Het. Chem.* 28:1025-1034.

International Search Report mailed on May 14, 2013, for PCT Patent Application No. PCT/HU2013/000009, filed on Feb. 1, 2013, three pages.

Son, J-K. et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.

Written Opinion of the International Searching Authority mailed on May 14, 2013, for PCT Patent Application No. PCT/HU2013/000009, filed on Feb. 1, 2013, three pages.

Abramenko et al. (1975). "Polymethine Dyes—Furo[2,3-g] Benzothiazole Derivatives," *Chemistry of Heterocyclic Compounds* 11:1361-1364.

Adams et al. (1951). Quinone imides. IV. P-Quinone monosulfonimides. Journal of the American Chemical Society 73:1145-1149.

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz et al. (2004). "Novel N-Aryl and N-Heteroaryl Sulfamide Synthesis via Palladium Cross Coupling," Organic Letters 6(16):2705-2708.

Ando et al. (1982). "Motion at the Active Site of Tosylchymotrypsin," *Journal of the American Chemical Society* 104(11):3172-3178.

Anjanappa et al. (2008). "2-(Trimethylsilyl)ethanesulfonyl amide as a new ammonia equivalent for palladium-catalyzed amination of aryl halides," Tetrahedron Letters 49:4585-4587.

Bartoli et al. (1991). "Unexpected Elimination to α,β-Alkynylketones in the Reaction of Dianions of 1-Arylenaminones with Trimethylchlorosilane," Tetrahedron Letters 32(48):7091-7092.

Batra et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli et al. (2004). "Application of Ionic Liquid Halide Nucleophilicity for the Cleavage of Ethers: A Green Protocol for the Regeneration of Phenols from Ethers," Journal of Organic Chemistry 69:3340-3344.

Bourgery et al. (1981). "Synthesis and Antiarrhythmic Activity of New Benzofuran Derivatives," Journal of Medicinal Chemistry 24(2):159-167.

Burton et al. (2003). "Palladium-Catalyzed Intermolecular Coupling of Aryl Chlorides and Sulfonamides under Microwave Irradiation," Organic Letters 5(23):4373-4376.

Castellino et al. (1984). "Synthesis of Benzofurans from Oxygenated Phenoxyamines," Journal of Organic Chemistry 49:4399-4404.

Chauhan et al. (2004). "Microwave assisted dealkylation of alkyl aryl ethers in ionic liquids," Journal of Chemical Research, pp. 693-694.

Cheng et al. (2007). "Facile Cleavage of Ethers in Ionic Liquid," Bulletin of the Chemical Society of Japan 80(10):2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507 , Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," *Current Topics in Catalysis* 6:19-33.

Fehnel (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

Groves (1972). "The Friedel—Crafts Acylation of Alkenes," Chem. Soc. Rev. 1:73-97.

Gutowski et al, (2005). "Prediction of the Formation and Stabilities of Energetic Salts and Ionic Liquids Based on ab Initio Electronic Structure Calculations," The Journal of Physical Chem. B 109:23196-23208.

Haddadin et al. (1976). "Reaction to Benzofurazan Oxide with Unsymmetrical 1, 3-Diketones: Steric Polar Effects," *Tetrahedron* 32:719-724.

Hauser et al. (1948) "Alkaline cleavage of unsymmetrical β-diketones. Ring opening of acylcyclohexanones to form Σ-acylcaproic acids," Journal of the Am. Chemical Society 70:4023-4026.

Headley et al. (2006). "Dynamic Solvation in Imidazolium-Based Ionic Liquids on Short Time Scales," Journal of Physical Chemistry 110:9549-9554.

Horton et al. (1967). "Reactions With Reactive Alkyl Halides," *J. Meth. In Enzymology* 11:556-565.

Ikawa et al. (2007). "Pd-Catalyzed Amidations of Aryl Chlorides Using Monodentate Biaryl Phosphine Ligands: A Kinetic, Computational, and Synthetic Investigation," Journal of the American Chemical Society 129:13001-13007.

(56) References Cited

OTHER PUBLICATIONS

Imori et al. (2006). "Efficient Demethylation of N,N-Dimethylanilines with Phenyl Chloroformate in Ionic Liquids," *Synlett.* 16:2629-2632.
Johnson Matthey Handbook of Pharmaceutical Catalysis, 2009, pp. 1-106.
Josh et al. (1986). "Some New Fluorinated β-Ketoamines and Their Copper Complexes," Synth. React. Inorg. Met. -Org. Chem. 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. El Sevior, pp. 448-449.
Kwiatkowski et al. (1978). "Metal Benzoylpivaloylmethanates, Part I. Free Ligands and Copper(II) Chelates," Transition Met. Chem. 3:305-308.
Laszlo et al. (1987). "Catalysis of Friedel-Crafts Alkylation by a Montmorillonite Doped with Transition-Metal Cations," Helvetica Chimica Acta 70:577-586.
Liu et al. (2004). "Cleavage of Methyl Ethers of Flavones by Chloroaluminate Ionic Liquid," Synthetic Communications 34:3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure*, 4$^{th}$ edition, Wiley Interscience, pp. 538-542.
March (Jul. 1, 1992). "Aliphatic Nucleophilic Substitution," Part 2 in *Advanced Organic Chemistry, Reactions Mechanism and Structure*, 4$^{th}$ edition, Wiley Interscience, pp. 442.
Marvel et al. (1941). "Diphenylacetic Acid," *Org. Synth. Coll.* vol. 1, 224-225.
Mehrotra et al. (2001). "Search for new chemical entities as menses inducing agents," Contraception. 64:187-191.
Munch et al. (1946). "The Preparation of Some α-Dialkylamino-ω-Methylaminoalkanes," *J. Am. Chem. Soc.* 68:1297-1299.
Nagy et al. (2007). "Isomorphous Substitution in Zeolites," *Mol. Sieves* 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.
Pal et al. (2007). "Synthesis of monohydroxy-functionalized triphenylene discotics: green chemistry approach," Tetrahedron 63:6874-6878.
Roshchin et al. (1998). "Synthesis of Benzofurans via Pd2+-Catalyzed Oxidative Cyclization of 2-Allylphenols," Journal of Organometallic Chemistry 560(1-2):163-167.
Sanfilippo (1988). "Synthesis of (aryloxy)alkylamines. 1. Novel antisecretory agents with H+K+-ATPase inhibitory activity," *J. Med. Chem.* 31(9):1778-1785.
Serajuddin (2007). "Salt formation to improve drug solubility," Advanced Drug Delivery Reviews 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry 208:234-237.
Skeels et al. (1989). "Zeolite Chemistry, Substitution of iron or titanium for Aluminum in Zeolites via reaction with the respective ammonium fluoride salts," *ACS Symposium series, zeolite Synth* 398:420-435.
Š lusarska et al. (Feb. 1981). "One-Pot Phase-Transfer-Catalysed N-Alkylation of Diphenylphosphinamide with Alcohols in the Presence of Methanesulfonyl Chloride," *Synthesis* 155-156.
Sun et al. (2004). "N-{2-[2-( 4-Phenylbutyl)benzofuran-4-yl]cyclopropylmethyl}-acetamide: an orally bioavailable melatonin receptor agonist," Bioorganic & Medicinal Chemistry Letters 14:5157-5160.
Tanaka (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber (1979). "Isosterism and molecular modification in drug design." Chem. Soc. Rev. 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman et al. (2005). "Recent advances in ether dealkylation," Tetrahedron 61:7833-7863.
Weitkamp et al. (1986). "Isomorphe Substitution in Zeolithen: Katalyse an Boro-, Alumo-und Galio-Silicaten mit ZSM-5-Strukter," *Chem. Ing. Tech.* 58(12):969-971 (with English Translation).
Wikipedia. (Nov. 5, 2012). "Reduction of Nitro Compounds."
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-based virtual screening for identification of novel 11 β-HSD1 inhibitors," European J. of Medicinal Chem. 44(3):1167-1171.
Yin et al. (2000). "Palladium-Catalyzed Intermolecular Coupling of Aryl Halides and Amides," Organic Letters 2(8):1101-1104.
Yin et al. (2002). "Pd-Catalyzed Intermolecular Amidation of Aryl Halides: The Discovery that Xantphos Can Be Trans-Chelating in a Palladium Complex," Journal of the Am. Chem. Soc. 124:6043-6048.
Zasshi (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al.
U.S. Appl. No. 14/403,528, filed Nov. 24, 2014, by Huszar et al.

* cited by examiner

PROCESS FOR THE PREPARATION OF DRONEDARONE BY OXIDATION OF A SULPHENYL GROUP

CROSS-REFERENCE TO RELATED APPLICATIONS

This application is a National Phase application under 35 U.S.C. §371 of International Application No. PCT/HU2013/000009 filed Feb. 1, 2013 and claims the benefit of EP Application No. 12462005.5 filed Feb. 14, 2012, the disclosures of which are incorporated herein by reference in their entirety.

FIELD OF THE INVENTION

The invention relates to a novel process for the preparation of dronedarone and pharmaceutically acceptable salts thereof, to novel intermediary compounds used in this process and their preparation.

TECHNICAL BACKGROUND

Dronedarone, i.e. N-[2-n-butyl-3-[4-[3-(di-n-butylamino) propoxy]benzoyl]-1-benzofuran-5-yl]-methanesulfonamide, having the formula (I):

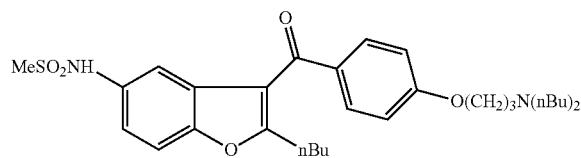

is a known drug for the treatment of arrhythmia (EP0471609).

There are some known processes for the preparation of dronedarone as follows:

In EP 0471609 the following scheme is disclosed for the preparation of dronedarone [Process A]

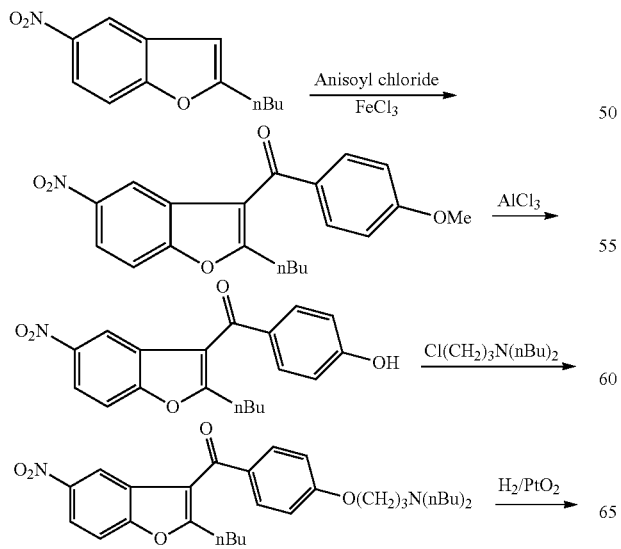

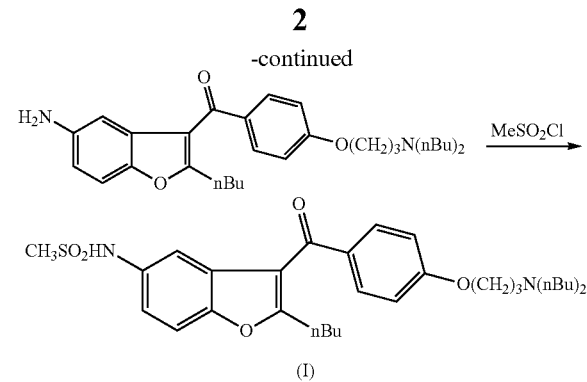

The above mentioned patent description discloses some new intermediary compounds, too.

In WO 02/48078 the following scheme is disclosed for the preparation of dronedarone [Process B]:

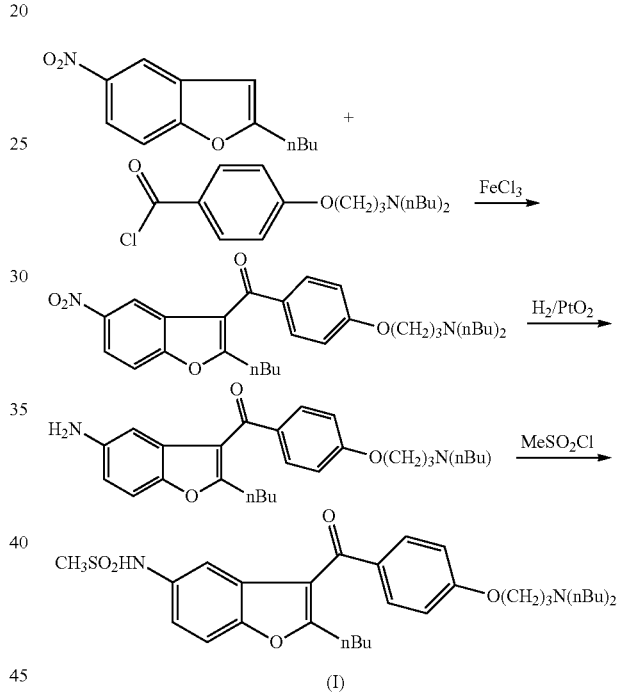

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so-called superconvergent route. In the first step of it 5-amino-2-butyl-benzofuran

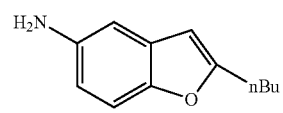

is mesylated and the obtained 2-butyl-5-methanesulfona-mido-benzofuran (in HCl salt form) is further reacted in the next step as follows:

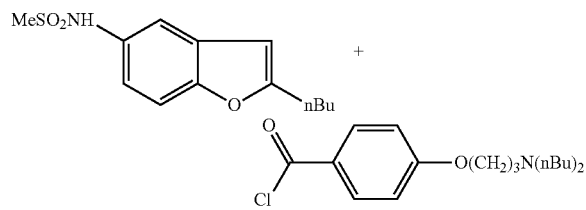

In this process the order of reaction steps are altered, the reduction and the methansulfonylation steps are performed at the beginning part of the procedure. Besides the reaction route for preparation of dronedarone, the starting material 2-butyl-5-methansulfonamido-benzofuran and its preparation are also claimed.

From among the mentioned procedures the first one [Process A] is the so-called linear synthesis. In this way of procedure the different parts of the dronedarone are stepwise built up on the starting compound. This method is the least economical because the continuous step by step building of the chemical groups is performed on more and more complicated and expensive molecules, which raises the costs of the preparation.

Furthermore it comprises complicated and harmful reaction steps because aluminium chloride is used in the cleaving reaction of the methoxy group which makes the industrial feasibility more complicated.

In WO 02/48078 (Process B) a shorter synthetic route is disclosed which makes this process more economical, but its last reaction step remained, the methansulfonylation reaction of the amino group. This reaction step (see the method described in example 6 of WO 02/48078) is complicated and gives a low yield of only 61.6%. Pure product can be expected after-purification using chromatographic column purification, which is necessary because of the separation difficulties of the bis-methanesulfonylated product.

The process disclosed in WO 02/48132 (process C) is simpler and more economical taking into consideration the number of the reaction steps. Unfortunately, in the last reaction step rather impure dronedarone.HCl (hydrochloride salt) is formed which is the obvious consequence of the presence of the dibutylamino group in the Friedel-Crafts reaction. According to Examples 3 and 4, the crude dronedarone hydrochloride salt is prepared with a yield of 90% which is further purified and finally the crude dronedarone base is produced with a yield of 86%. This base is reacted with hydrogen chloride gas dissolved in isopropanol which results in pure dronedarone hydrochloride salt. No yield is given for this reaction step. According to example 5 crude dronedarone hydrochloride salt is prepared with a yield of 90%, which is washed with water and reacted with hydrogen chloride gas dissolved in isopropanol, resulting dronedarone hydrochloride salt again. The quality of this product is not known. However, since neither the components used in the Friedel-Crafts reaction nor the resulting products and by-products are soluble in water, the washing step with water cannot result any purification apart from the removal of inorganic salts.

There is another drawback of this process, namely, a dimesylated side-product is formed in the mesylation reaction of the 5-amino-2-butyl-benzofuran. The purification is carried out by crystallization which has a yield of 78.5%.

It is an object of the present invention to provide a novel process for the preparation of dronedarone (I), starting from known and commercially available materials, applying simple, environmentally compatible reagents and solvents, to afford high overall yields and good purity of the product.

SUMMARY OF THE INVENTION

The main aspect of the invention is a process for the preparation of dronedarone (I) and pharmaceutically acceptable salts thereof

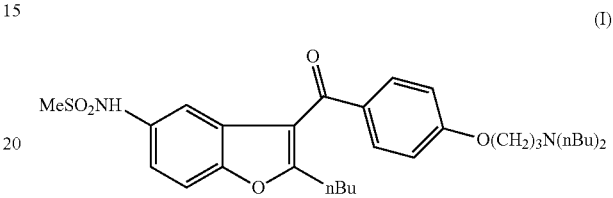

which comprises oxidizing a compound of formula (IV) or a salt thereof

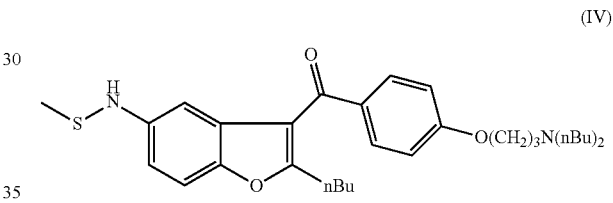

with an oxidizing agent in organic or inorganic solvents, isolating the obtained product as a base and, if desired, converting it into a pharmaceutically acceptable salt.

We have surprisingly found that performing the mesylation of the amino group at the end of the synthesis by the oxidation of a sulfenyl group, instead of using mesyl chloride, has several advantages.

Also in this process (as in the above mentioned process [A] and process [B]) the methanesulfonylation of the amino group is the last step but the reagent is very simple and readily available from commercial sources. Although the product should be purified by column chromatography, the obtained isolated yield is better than in the above mentioned patents.

Further aspects of the invention include the compound of formula (IV) and pharmaceutically acceptable salts thereof as a new compound and a process for the preparation thereof (see below in the "Detailed description of the invention" part).

DETAILED DESCRIPTION OF THE INVENTION

Therefore the present invention relates to a process for the preparation of dronedarone and pharmaceutically acceptable salts thereof. The whole process—starting from compounds available from commercial sources—reads as follows:

(a) reacting a compound of formula (II) (methanesulfenyl chloride)

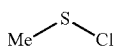
(II)

with a compound of formula (III) ((5-amino-2-butyl-benzofuran-3-yl)-[4-(3-dibutylamino-propoxy)-phenyl]-methanone)

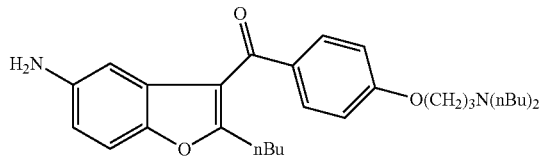
(III)

optionally in the presence of a base catalyst to obtain a compound of formula (IV):

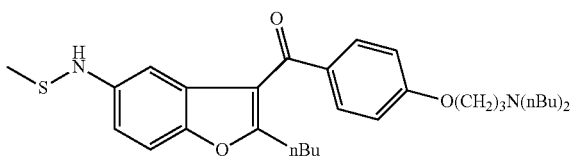
(IV)

(b) oxidation of compound (IV) ((2-butyl-5-methylsulfanylamino-benzofuran-3-yl)-[4-(3-dibutylamino-propoxy)-phenyl]-methanone) obtained in step (a) above or a salt thereof to obtain dronedarone (I), isolating the obtained product as a base and, if desired, converting it into a pharmaceutically acceptable salt.

Compound of formula (II) can be purchased or can be prepared by known methods (JACS 1989, 111, 1363; J. Org. Chem. 1959, 24, 2004; J. Het. Chem. 1991, 28, 1025. Compound of formula (III) is known from WO 02/48132 (Sanofi).

The intermediary compound of formula (IV) is a new compound. Said compound, its salts and the preparation process thereof (i.e. the above step (a)) form further objects of the invention. Said compound is isolated in pure form during the synthesis of dronedarone.

The reaction of step (a) is typically carried out in a solvent or in a mixture of solvents, optionally in the presence of a base catalyst.

The solvent in this step is typically selected from the group of alcohols, amides, aromatic solvents and any mixtures thereof. Specific examples include, among others, methanol, ethanol, pyridine and DMF.

In general, said base catalyst is an organic or inorganic base. Said base catalyst is typically selected from the group of alkali, alkoxides, e.g. sodium methoxide, and nitrogen-containing bases, e.g. pyridine and 2-methylpyridine. If we use a basic solvent, e.g. pyridine, no further addition of base catalyst is needed:

The oxidation of step (b) is carried out in a solvent, using an oxidizing agent.

The solvent in this step is typically selected from the group of alcohols, ketones, esters, amides, chlorinated solvents, aromatic solvents, inorganic acids and any mixtures thereof. Specific examples include, among others, dichloromethane, ethanol, acetone, ethyl acetate and acetic acid.

In general, said oxidizing agent is selected from the generally used organic and inorganic oxidizing agents. Examples for such oxidizing agents include hydrogen peroxide and peroxy carboxylic acids, such as meta-chloroperbenzoic acid (MCPBA), peracetic acid, pertrifluoroacetic acid and hypochlorites, such as sodium hypochlorite.

In the above reactions the temperature is chosen according to the general practice of a person skilled in organic chemistry. Typically the temperature is between 0° C. and the boiling point of the applied solvent (or solvent mixture).

Applicable temperature values can be found in the examples. In general, step (a) is carried out at 0-20° C. and step (b) is conveniently carried out at room temperature.

Both reaction steps are generally carried out under atmospheric pressure.

In the processes for the preparation of the intermediary compound of formula (IV) the product is typically isolated as a base. If desired, the isolated base can be converted into a salt (acid addition salt) thereof, which is typically a pharmaceutically acceptable salt (possible acids are mentioned below). Theoretically the acid addition salt can be prepared directly if the relating acid is in the final reaction mixture from which the solid product is made (however, this way is not applied in case of these compounds where the base type form has practical importance).

The applicable acid for the preparation of pharmaceutically acceptable salts can be any inorganic or organic acid which forms an acid addition salt with the compound of general formula (I) or (IV). Exemplary acids which can form an acid addition salt are as follows: acetic acid, adipic acid, alginic acid, ascorbic acid, aspartic acid, benzoic acid, benzenesulfonic acid, boric acid, butyric acid, citric acid, ethanesulfonic acid, fumaric acid, hydrogen chloride, hydrogen bromide, hydrogen iodide, 2-hydroxyethanesulfonic acid, maleic acid, oxalic acid, methanesulfonic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compound of general formula (I) (see the "left side" of the molecule) a salt formation can be carried out (on the amide part of it) by a strong base, e.g. an alkaline hydroxide, typically by sodium hydroxide. However, these salts have less practical importance, but they are within the scope of salts. It means that the phrase "salts" embraces both the acid addition salts and the salts formed by bases (basic salts) in case of compounds of general formula (I).

In the examples the following HPLC method was applied for the determination of the purity of the reaction products:
Column: Waters Symmetry C18 4.6×150 mm, 5 µm
Mobile phases:
Mobile phase A: 5 mM sodium phosphate buffer, pH=2.2
Mobile phase B: acetonitrile
Mobile phase C: methanol
Column temp.: 25° C.
Auto sampler temp.: 20° C.
Gradient:

| Time (min) | A (%) | B (%) | C (%) |
|---|---|---|---|
| 0 | 65 | 30 | 5 |
| 20 | 40 | 50 | 10 |
| 45 | 15 | 75 | 10 |
| 47 | 65 | 30 | 5 |
| 57 | 65 | 30 | 5 |

Injection vol: 10 µL
Flow rate: 1.5 mL/min

Run time: 57 min
Detection: 245 nm

EXAMPLES

Example 1

(2-butyl-5-methylsulfanylamino-benzofuran-3-yl)-
[4-(3-dibutylamino-propoxy)phenyl]-methanone
(IV)

1.98 g of methanesulfenyl chloride (II) (0.024 mol, 1.2 eq; freshly prepared as described in the above mentioned literature), 9.57 g of (5-amino-2-butyl-benzofuran-3-yl)-[4-(3-dibutylamino-propoxy)-phenyl]-methanone (III) (0.02 mol, 1 eq) and 10 mL of 1.5 M sodium methylate methanolic solution were added into a flask and the mixture was diluted with 50 mL of methanol. The reaction mixture was stirred for 3 hours at room temperature. After the reaction was complete (followed by HPLC) the mixture was poured into 150 mL of water. The product was extracted with 2×60 mL of dichloromethane. The organic phase was washed with 50 mL of aq. $NaHCO_3$ solution and then with 50 mL of water. The solvent was evaporated and the product was purified by column chromatography (column: spheric silica (60 Å); eluent: toluene: MTBE:methanol=50:40:10) to obtain 9.14 g of compound (IV) (87%) as a light yellow oil.

Purity by HPLC: 99.4%.
Molecular weight (calc): 524.7599 Da; (measured): 524.7592 Da
$^1$H NMR (DMSO): 7.81 (d, J=8.6 Hz, 2H); 7.30 (m, 3H); 7.05 (d, J=8.6 Hz, 2H); 5.61 (s, 1H); 4.05 (t, J=6.0 Hz, 2H); 2.92 (s, 3H); 2.78 (t, J=7.0 Hz, 2H); 2.55 (t, J=7.1 Hz, 2H); 2.39 (t, J=7.1 Hz, 4H); 1.90 (m, 2H); 1.70 (m, 2H); 1.4 (m, 10H); 0.9 (m, 9H).

Example 2

(2-butyl-5-methylsulfanylamino-benzofuran-3-yl)-
[4-(3-dibutylamino-propoxy)-phenyl]-methanone
(IV)

4.78 g of (5-amino-2-butyl-benzofuran-3-yl)-[4-(3-dibutylamino-propoxy)-phenyl]-methanone (III) (0.01 mol, 1 eq) and 35 mL of pyridine were placed into a flask. The mixture was cooled down to 0° C. and 0.99 g of methanesulfenyl chloride (II) (0.012 mol, 1.2 eq; freshly prepared as described in the above mentioned literature) was added in 10 min. The mixture was stirred at 0° C. for 3 hours and then heated to room temperature and stirred for 6 hours. The mixture was poured into 100 mL of water. The product was extracted with 50 mL of dichloromethane. The organic phase was washed with 30 mL of water. The solvent was evaporated and the product was purified by column chromatography (column: spheric silica (60 Å); eluent: toluene:ethyl acetate=70:30) to obtain 2.2 g of compound (IV) (42%) as a light yellow oil.

Purity by HPLC: 98.1%.
The product was identical with the compound prepared in Example 1.

Example 3

N-[2-butyl-3-[4-[3-(dibutylamino)propoxy]benzoyl]-
1-benzofuran-5-yl]-methanesulfonamide (I)

5.27 g of MCPBA (0.022 mol, 1.1 eq) and 10.49 g of (2-butyl-5-methylsulfanylamino-benzofuran-3-yl)-[4-(3-dibutylamino-propoxy)-phenyl]-methanone (IV) (0.02 mol, 1 eq) were dissolved in 90 mL of dichloromethane. The reaction mixture was stirred at room temperature for 4 hours. After the reaction was completed (followed by HPLC) 50 mL of 5% NaOH solution was added and the mixture was stirred for 30 min. The phases were separated and the aqueous phase was extracted with 30 mL of dichloromethane. The combined organic phase was washed with 50 mL of water, dried and concentrated. The crude product was purified by column chromatography (column: spheric silica (60 Å); eluent: toluene:ethyl acetate-70:30) to obtain 9.24 g of dronedarone (I) (83%).

Purity by HPLC: 99.7%.
$^1$H NMR (DMSO): 7.77 (d, J=8.5 Hz, 2H); 7.27 (m, 3H); 6.91 (d, J=8.5 Hz, 2H); 5.52 (bs, 1H); 4.05 (t, J=6.0 Hz, 2H); 2.87 (s, 3H); 2.78 (t, J=7.0 Hz, 2H); 2.55 (t, J=7.0 Hz, 2H); 2.39 (t, J=7.0 Hz, 4H); 1.90 (m, 2H); 1.70 (m, 2H); 1.3-1.4 (m, 10H); 0.8-0.9 (m, 9H).

Example 4

N-[2-butyl-3-[4-[3-(dibutylamino)propoxy]benzoyl]-
1-benzofuran-5-yl]-methanesulfonamide (I)

10.49 g of (2-butyl-5-methylsulfanylamino-benzofuran-3-yl)-[4-(3-dibutylamino-propoxy)-phenyl]-methanone (IV) (0.02 mol, 1 eq) was dissolved in 40 mL of glacial acetic acid. 20 mL of 30% hydrogen peroxide solution was added in 1 hour at room temperature and the reaction mixture was stirred for 48 hours. 100 mL of water was added to the reaction mixture and the product was extracted with 60 mL of dichloromethane. The organic phase was concentrated and the crude product was purified by column chromatography (column: spheric silica (60 Å); eluent: toluene:ethyl acetate=70:30) to obtain 8.24 g of dronedarone (I) (74%).

Purity by HPLC: 99.4%.
The product was identical with the compound prepared in Example 3.

The invention claimed is:
1. A process for the preparation of dronedarone (I), or a pharmaceutically acceptable salt thereof,

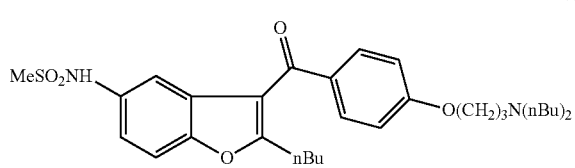

comprising the steps of:
a) oxidizing a compound of formula (IV), or a salt thereof,

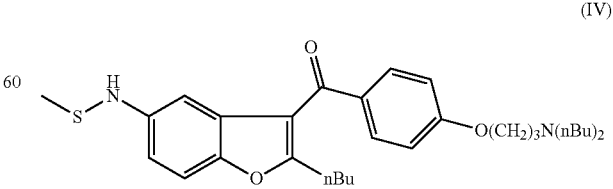

with an oxidizing agent in an organic or inorganic solvent or solvent mixture;

b) isolating dronedarone (I); and
c) optionally converting dronedarone (I) into a pharmaceutically acceptable salt thereof.

2. The process of claim 1 where the oxidizing agent is selected from the group consisting of hydrogen peroxide, a peroxy carboxylic acid and a hypochlorite.

3. The process of claim 1 where step a) is carried out at room temperature.

4. A compound of formula (IV), or a salt thereof,

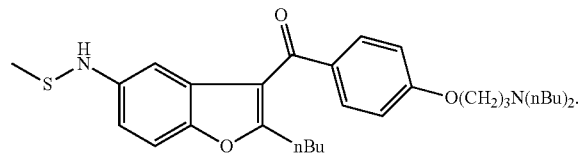

(IV)

5. A process for the preparation of a compound of formula (IV), or a salt thereof,

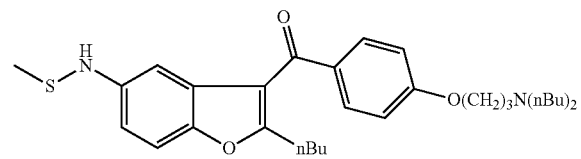

(IV)

comprising the steps of:
a) reacting a compound of formula (III)

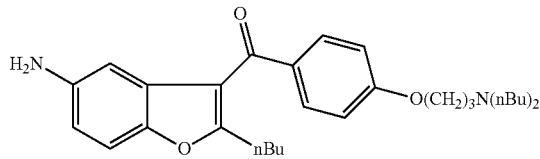

(III)

with a compound of formula (II)

(II)

b) isolating the compound of formula (IV); and
c) optionally converting the compound of formula (IV) into a salt thereof.

6. The process of claim 5 where the reaction is carried out in the presence of an organic or inorganic base catalyst.

7. The process of claim 1, further comprising a process for the preparation of the compound of formula (IV) wherein:
a compound of formula (III)

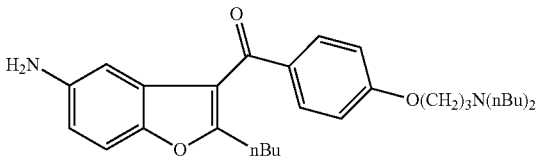

(III)

is reacted with a compound of formula (II)

(II)

to obtain the compound of formula (IV).

8. The process of claim 7 where the oxidizing agent in step a) is selected from the group consisting of hydrogen peroxide, a peroxy carboxylic acid and a hypochlorite.

9. The process of claim 7 where step a) is carried out at room temperature.

10. The process of claim 7 where the reaction of the compound of formula (III) with the compound of formula (II) is carried out in the presence of an organic or inorganic base catalyst.

\* \* \* \* \*